United States Patent
Saito

(10) Patent No.: US 10,772,483 B2
(45) Date of Patent: Sep. 15, 2020

(54) IMAGING APPARATUS

(71) Applicant: OLYMPUS CORPORATION, Tokyo (JP)

(72) Inventor: Saeri Saito, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/795,606

(22) Filed: Oct. 27, 2017

(65) Prior Publication Data
US 2018/0042450 A1 Feb. 15, 2018

Related U.S. Application Data

(63) Continuation of application No. PCT/JP2016/055078, filed on Feb. 22, 2016.

(30) Foreign Application Priority Data

Aug. 7, 2015 (JP) .................................. 2015-157110

(51) Int. Cl.
*A61B 1/00* (2006.01)
*G02B 23/24* (2006.01)
(Continued)

(52) U.S. Cl.
CPC .......... *A61B 1/0005* (2013.01); *A61B 1/0002* (2013.01); *A61B 1/00006* (2013.01);
(Continued)

(58) Field of Classification Search
CPC .............. A61B 1/0005; A61B 1/00006; A61B 1/00009; A61B 1/0002; A61B 1/04;
(Continued)

(56) References Cited

U.S. PATENT DOCUMENTS 5,995,136 A * 11/1999 Hattori ............... G02B 23/2484
    348/269
6,002,425 A * 12/1999 Yamanaka ............. H04N 5/335
    348/68
(Continued)

FOREIGN PATENT DOCUMENTS

EP     2 575 354 A1    4/2013
JP     2007-295096 A   11/2007
(Continued)

OTHER PUBLICATIONS

English translation of International Preliminary Report on Patentability dated Feb. 22, 2018 together with the Written Opinion received in related International Application No. PCT/JP2016/055078.

(Continued)

*Primary Examiner* — Thai Q Tran
*Assistant Examiner* — Sunghyoun Park
(74) *Attorney, Agent, or Firm* — Scully, Scott, Murphy & Presser, P.C.

(57) ABSTRACT

An imaging apparatus includes an imaging element that outputs a video signal and to which a processor drive clock is input from an external image processor. The imaging apparatus father includes a clock generation circuit and a memory. The clock generation circuit generates a clock synchronized with the video signal output from the imaging element. The memory stores the video signal output from the imaging element in synchronization with the clock synchronized with the video signal and outputs the stored video signal in synchronization with the processor drive clock.

13 Claims, 8 Drawing Sheets

(51) Int. Cl.
*A61B 1/045* (2006.01)
*A61B 1/04* (2006.01)
*H03L 7/08* (2006.01)
*H04N 5/372* (2011.01)
*H04N 5/374* (2011.01)

(52) U.S. Cl.
CPC ............ *A61B 1/00009* (2013.01); *A61B 1/04* (2013.01); *A61B 1/045* (2013.01); *G02B 23/24* (2013.01); *H03L 7/0807* (2013.01); *H04N 5/372* (2013.01); *H04N 5/374* (2013.01)

(58) Field of Classification Search
CPC ....... A61B 1/045; G02B 23/24; H03L 7/0807; H04N 5/372; H04N 5/374
See application file for complete search history.

(56) References Cited

U.S. PATENT DOCUMENTS

| | | |
|---|---|---|
| 2004/0061776 A1 | 4/2004 | Mochida et al. |
| 2004/0085462 A1* | 5/2004 | Sasaki .................. G06T 1/20 348/231.6 |
| 2006/0020214 A1* | 1/2006 | Mori ..................... A61B 1/04 600/478 |
| 2009/0213212 A1* | 8/2009 | Nakamura ............ A61B 1/042 348/65 |
| 2009/0290018 A1 | 11/2009 | Abe |
| 2011/0050874 A1* | 3/2011 | Reshef .................. H04N 5/374 348/65 |
| 2013/0016199 A1 | 1/2013 | Kobayashi et al. |

FOREIGN PATENT DOCUMENTS

| | | |
|---|---|---|
| JP | 2009-514600 A | 4/2009 |
| JP | 2013-000452 A | 1/2013 |
| JP | 2013-22054 A | 2/2013 |
| JP | 2015-80702 A | 4/2015 |
| WO | 2007/056104 A2 | 5/2007 |

OTHER PUBLICATIONS

International Search Report dated May 24, 2016 received in PCT/JP2016/055078.
Japanese Office Action dated Apr. 25, 2017 received in JP 2017-507901.
Chinese Office Action dated Oct. 22, 2018 in Chinese Patent Application No. 201680025787.4.
Chinese Office Action dated Jul. 3, 2019 in Chinese Patent Application No. 201680025787.4.
Extended Supplementary European Search Report dated Jan. 4, 2019 in European Patent Application No. 16 83 4830.8.

* cited by examiner

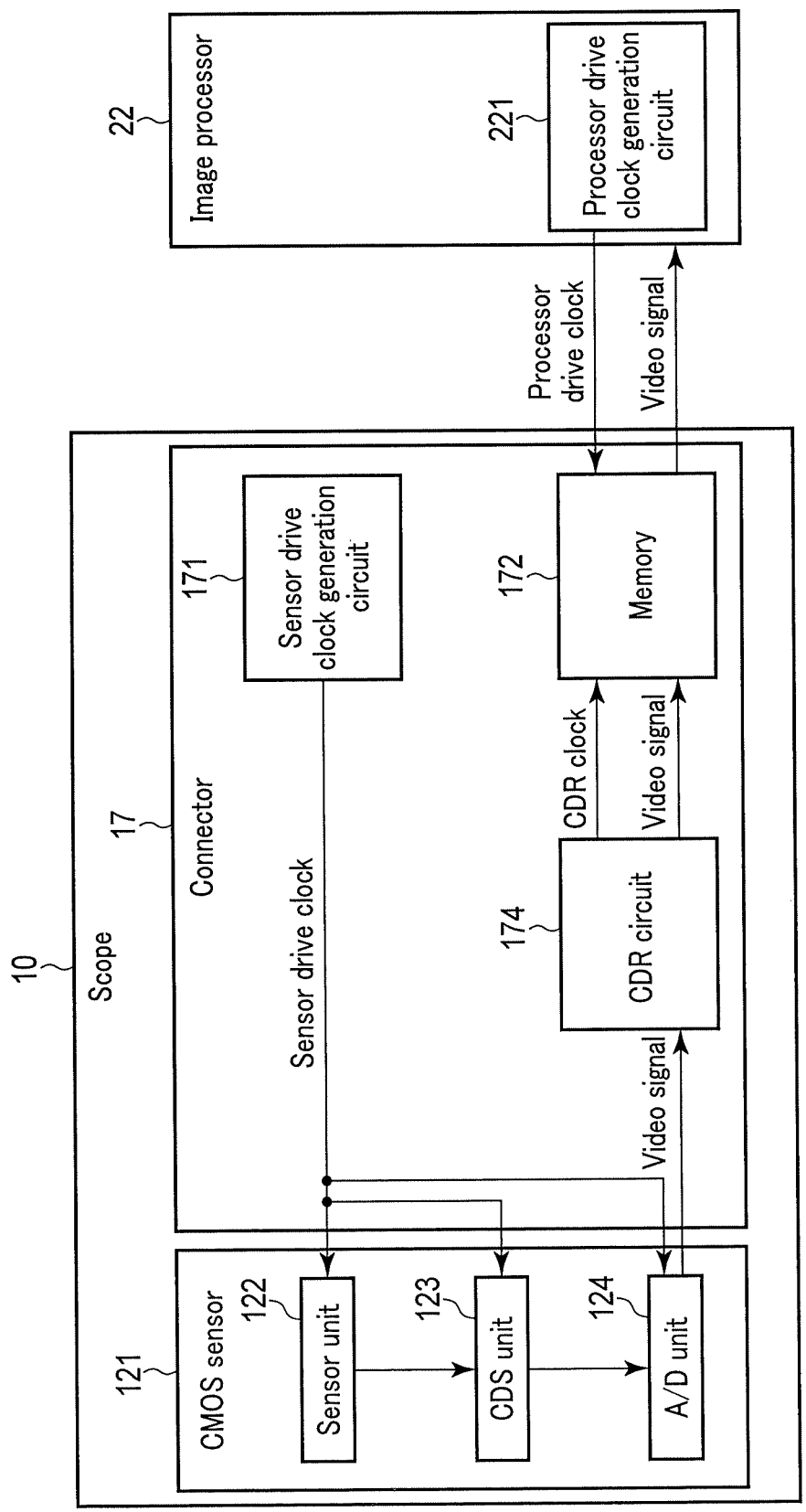
F I G. 5

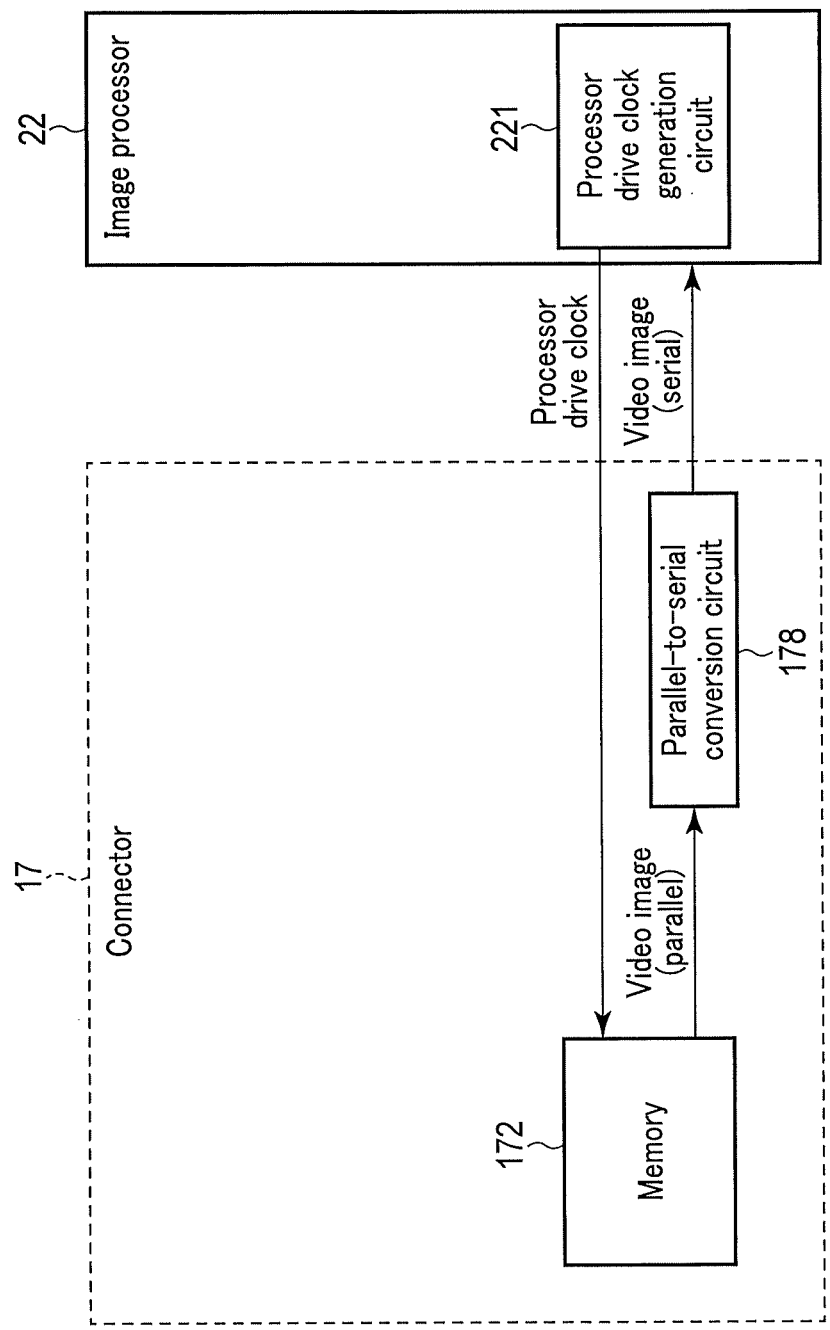
F I G. 7

IMAGING APPARATUS

CROSS-REFERENCE TO RELATED APPLICATIONS

This application is a Continuation Application of PCT Application No. PCT/JP2016/055078, filed Feb. 22, 2016 and based upon and claiming the benefit of priority from the prior Japanese Patent Application No. 2015-157110, filed Aug. 7, 2015, the entire contents of both of which are incorporated herein by reference.

BACKGROUND OF THE INVENTION

1. Field of the Invention

The present invention relates to an imaging apparatus.

2. Description of the Related Art

In recent years, performance of an imaging element has been highly advanced in an imaging apparatus such as an endoscope and an extracorporeal camera. Conventionally, the imaging element was controlled in synchronization with a clock that is input from a processor, but with improved performance, it has been recently controlled in synchronization with a clock that is independent from the processor. Such a configuration requires a clock changing to synchronize an imaging operation by the imaging element with a display operation by the processor. For the technique of changing clocks, Jpn. Pat. Appln. KOKAI Publication No. 2013-000452 discloses the electronic endoscope apparatus configured to generate the display clock from the transmission clock transmitted from the scope distal end to the image processor and to perform display in accordance with the generated display clock. The electronic endoscope apparatus of Jpn. Pat. Appln. KOKAI Publication No. 2013-000452 is further configured to generate the imaging clock from the transmission clock transmitted from the image processor to the scope distal end and to perform imaging in accordance with the imaging clock generated.

BRIEF SUMMARY OF THE INVENTION

According to an aspect of the invention, an imaging apparatus that includes an imaging element that outputs a video signal and to which a processor drive clock is input from an external image processor, the imaging apparatus comprises: a clock generation circuit that generates a clock synchronized with the video signal output from the imaging element; and a memory that stores the video signal output from the imaging element in synchronization with the clock synchronized with the video signal and outputs the stored video signal in synchronization with the processor drive clock.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 shows a main configuration of the endoscope system according to Modification 3.

FIG. 7 shows a configuration of a connector according to Modification 5.

DETAILED DESCRIPTION OF THE INVENTION

Figure 1:
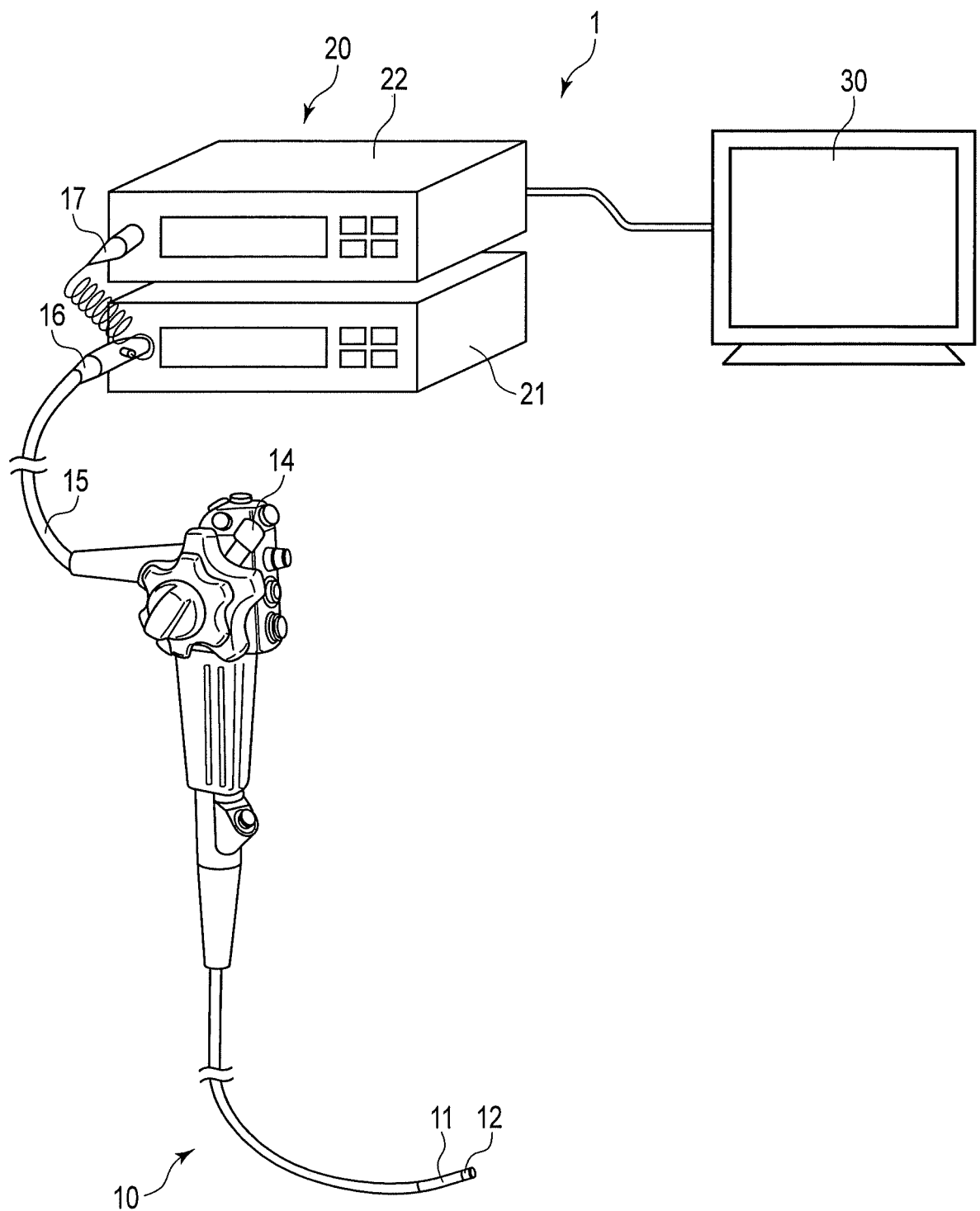
FIG. 1 schematically shows the structure of an endoscope system including an imaging apparatus according to one embodiment of the present invention.

Embodiments of the present invention will be described with reference to the accompanying drawings. FIG. 1 schematically shows the structure of an endoscope system including an imaging apparatus according to one embodiment of the present invention. An endoscope system 1 of FIG. 1 includes a scope 10, a controller 20, and a monitor 30. The scope 10 transmits a video signal inside the subject body to an image processor 22 of the controller 20. The image processor 22 processes the video signal transmitted from the scope 10. The monitor 30 displays the video based on the video signal processed by the controller 20.

The scope 10 that functions as the imaging apparatus in the present embodiment includes an insertion section 11, an operation unit 14, a cable 15, a connector 16, and a connector 17.

The insertion section 11 is a section inserted into the subject body. An imaging element 12 is arranged inside the distal end of the insertion section 11. The imaging element 12 is a CMOS sensor or a CCD sensor and is configured to image an interior of the subject body in synchronization with the sensor drive clock to generate the video signal relating to the subject body. The insertion section 11 is further configured to emit illumination light from the distal end.

The insertion section 11 includes a portion configured to bend in response to operation of an operation knob at the operation unit 14 performed by an operator such as a doctor, and a portion configured to bend passively by external force, not by operation of the operation unit 14.

The operation unit 14 connects the insertion section 11 and the cable 15. The operation unit 14 includes an RL knob for bending the insertion section 11 rightward or leftward, and a UD knob for bending the insertion section 11 upward or downward. The operation unit 14 includes various switches.

A light guide is arranged inside the insertion section 11, the operation unit 14, and the cable 15. The light guide is connected to a light source apparatus 21 of the controller 20 via the connector 16 provided at the proximal end of the cable 15. Various signal lines are arranged inside the insertion section 11, the operation unit 14, and the cable 15. The signal lines are connected to an image processor 22 of the controller 20 via the connector 17 that is connected to the connector 16.

The light source apparatus 21 includes a light source such as a white LED, and emits illumination light. The illumination light emitted from the light source apparatus 21 is transmitted to the distal end of the insertion section 11 via the light guide and emitted from the distal end of the insertion section 11. The interior of the subject body is illuminated accordingly.

The image processor 22 processes the video signal obtained by the imaging element 12 of the insertion section 11. This processing includes the processing of converting to a format where the video signal can be displayed on the monitor 30, e.g., gradation correction processing, etc. The image processor 22 generates a processor drive clock and inputs the generated processor drive clock to the connector 17 and the monitor 30. The processor drive clock may or may not be synchronized with the sensor drive clock.

In FIG. 1, the image processor 22 and the light source apparatus 21 are arranged independently in the controller 20, but they may be configured as a single housing.

The monitor 30 is, for example, a liquid crystal monitor. The monitor 30 displays video and various kinds of information based on the video signal processed by the image processor 22, in synchronization with the processor drive clock generated by the image processor 22.

Figure 2:
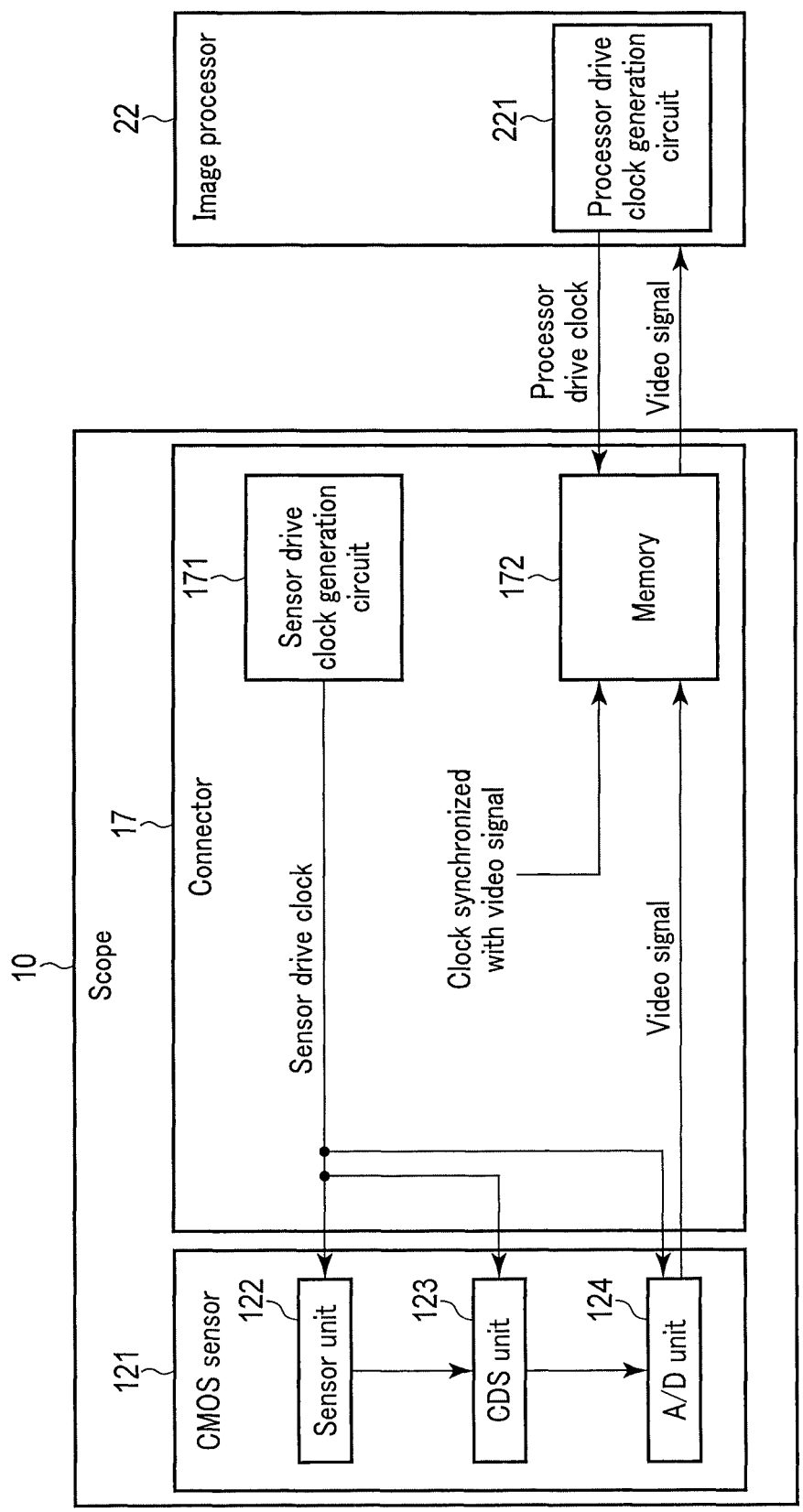
FIG. 2 shows a main configuration of an endoscope system according to one embodiment of the present invention.

FIG. 2 shows a main configuration of an endoscope system 1 according to the present embodiment. As described above, the imaging element 12 performs an imaging operation in accordance with the sensor drive clock that is independent of the processor drive clock generated by the image processor 22. In the present embodiment, the clock change is performed at the connector 17 to synchronize the imaging operation by the imaging element 12 and the display operation by the monitor 30.

In the present embodiment, the clock change processing and the like are carried out at the connector 17, but a similar function may be provided at any other portions in the scope, e.g., the connector 16 or the operation unit 14.

The first example is an example of the configuration in which the imaging element 12 is a CMOS sensor 121. The CMOS sensor 121 includes a sensor unit 122, a correlated double sampling (CDS) unit 123, and an A/D unit 124.

The sensor unit 122 includes pixels arranged two dimensionally. Each pixel is formed, for example, by a photodiode, and outputs an analog electronic signal (video signal) in accordance with incident light. The CDS unit 123 performs processing of removing a reset noise component (dark current component) in the video signal output from the sensor unit 122. The A/D unit 124 converts the video signal, output sequentially from the CDS unit 123, to a digital signal. In the CMOS sensor 121, the sensor drive clock controls signal accumulation and signal readout of each pixel. For example, in the case where exposure of the CMOS sensor is controlled by a rolling shutter method, the exposure time of pixels at each row of the sensor unit 122 is controlled in accordance with the sensor drive clock.

The connector 17 includes a sensor drive clock generation circuit 171 and the memory 172.

The sensor drive clock generation circuit 171 is a circuit that generates a sensor drive clock necessary for driving the CMOS sensor 121. The sensor drive clock is generated by multiplying/dividing a basic clock having a predetermined frequency, for example.

The memory 172 is a memory that temporarily stores a digital video signal output from the CMOS sensor 121. The memory 172 includes two clock input terminals, and is a memory in which the video signal is written using the clock synchronized with the video signal as a writing clock and from which the video signal is read out using the processor drive clock as a readout clock. Details of the "clock synchronized with the video signal" will be described later. Examples of the memory 172 include a line memory capable of storing a video signal for one row output from the A/D unit 124. This is because, in general, the video signal is output from the CMOS sensor 121 on a row-by-row basis. For the memory 172, a frame memory such as SRAM can be used. The controls of writing to and reading from the memory may be performed by generating a writing address and reading address, or by using a memory that operates as FIFO.

The image processor 22 includes a processor drive clock generation circuit 221. The processor drive clock generation circuit 221 is a circuit for generating a processor drive clock necessary for driving the image processor 22 and the monitor 30. The image processor 22 specifies a vertical position and a horizontal position of the video signal transmitted from the scope 10 and performs image processing in accordance with the processor drive clock. The processor drive clock is generated by multiplying/dividing a basic clock having a predetermined frequency, for example. The frequency of the basic clock for generating the processor drive clock and the frequency of the basic clock for generating the sensor drive clock may be the same or different.

Hereinafter, a description will be given of operations of the endoscope system 1 according to the present embodiment. First, the scope 10, the light source apparatus 21 and the image processor 22 of the endoscope system 1 are powered on. At this time, the sensor drive clock generation circuit 171 of the scope 10 inputs the sensor drive clock to the imaging element 12 (CMOS sensor 121). The CMOS sensor 121 controls exposure of each pixel row of the sensor unit 122 in accordance with the sensor drive clock. The video signal is output from the sensor unit 122 each time the exposure of each pixel row is ended. The reset noise of the video signal output from the sensor unit 122 is removed at the CDS unit 123. The video signal output from the CDS unit 123 is converted into a digital signal by the A/D unit 124, and is output. The video signal from the CMOS sensor 121 is serially transmitted, for example. In this case, the frequency of the transmission clock of the video signal can be different from the frequency of the sensor drive clock. At this time, the "clock synchronized with the video signal" is a clock in which the sensor drive clock is multiplied/divided. Specific examples of the clock synchronized with the video signal will be explained later.

The memory 172 starts writing of the video signal output from the CMOS sensor 121 in synchronization with the start of the output of the video signal from the CMOS sensor 121. That is, the memory 172 stores the video signal to be output in a pixel row unit basis from the CMOS sensor 121 in accordance with the input of the clock synchronized with the video signal. The writing of the video signal in the memory 172 is performed in synchronization with the clock synchronized with the video signal. Because the clock synchronized with the video signal is in synchronization with the sensor drive clock, the imaging operation by the CMOS sensor 121 and the writing operation of the video signal to the memory 172 are synchronized.

On the other hand, the processor drive clock generation circuit 221 of the image processor 22 inputs the processor drive clock to the memory 172. The memory 172 outputs the stored video signal in accordance with the input of the processor drive clock. Reading out the video signal from the memory 172 is performed in synchronization with the processor drive clock. That is, the clock synchronized with the video signal output from the memory 172 is changed to the processor drive clock.

The image processor 22 specifies a vertical position and a horizontal position in the video signal in accordance with the processor drive clock and applies image processing to the video signal. The image processor 22 outputs the video signal subjected to the image processing to the monitor 30 in synchronization with the processor drive clock.

The monitor 30 displays the video based on the video signal output from the image processor 22 in synchronization with the processor drive clock.

According to the embodiment described above, the memory 172 is used to change the "clock synchronized with the video signal" to the processor drive clock. Thus, even when the imaging element 12 (CMOS sensor 121) uses the clock having a frequency different from that of the image processor 22, synchronization between the imaging operation and the display operation is maintained. Furthermore, even when there is a need to drive the imaging element 12 (CMOS sensor 121) with a clock of higher accuracy than the processor drive clock output from the image processor 22, the requirement of the imaging element 12 can be met. According to the present embodiment, the memory 172 is provided in the scope 10, not the image processor 22. Therefore, the configuration of the image processor 22 can be simplified. Furthermore, because the video signal output from the scope 10 is in synchronization with the processor drive clock, the image processor 22 does not have to include a receiving circuitry for receiving various types of video signals of different frequencies. From this aspect also, the configuration of the image processor 22 can be simplified.

A description will be given of modifications of the present embodiment.

Modification 1

Figure 3:
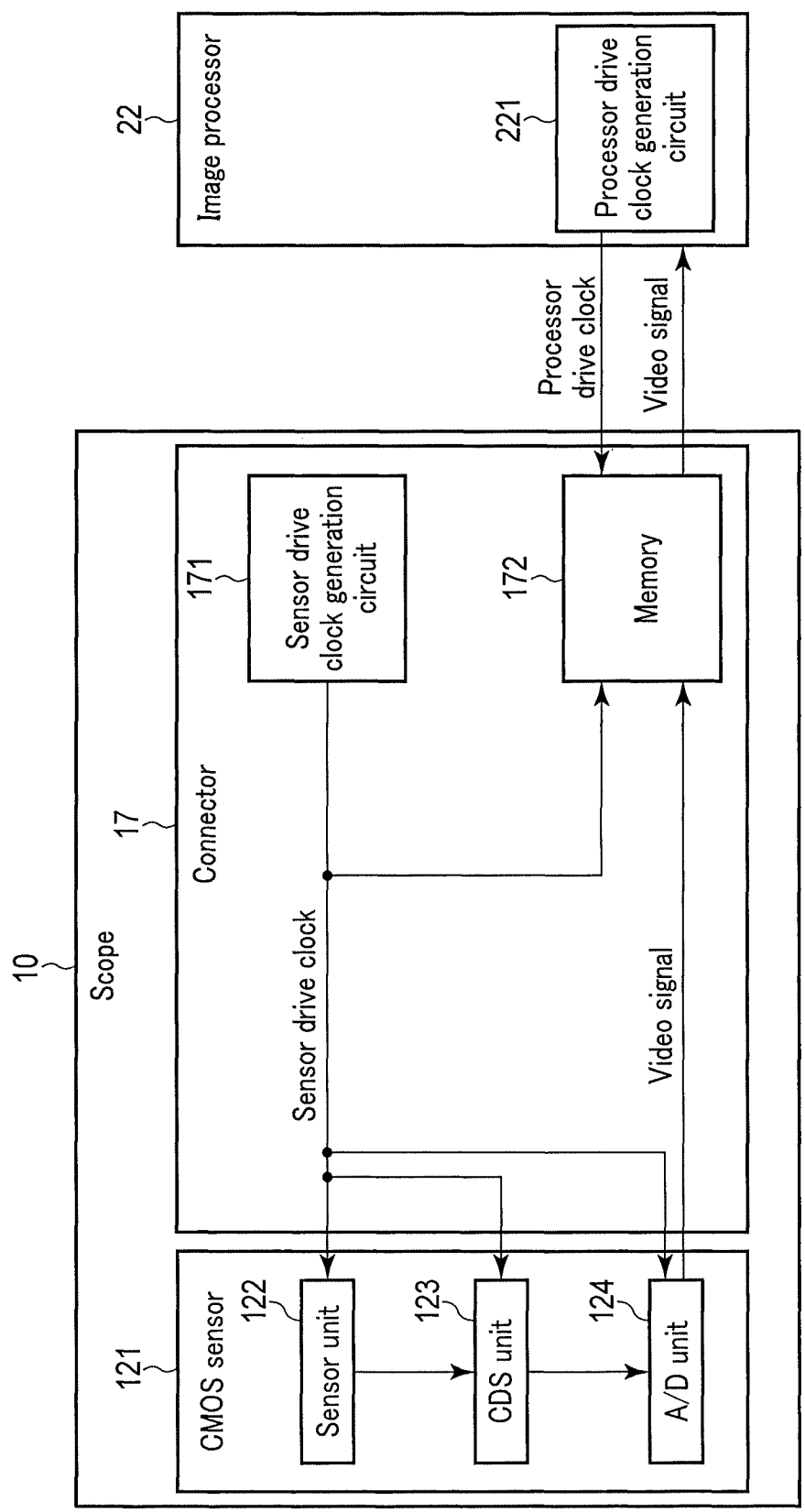
FIG. 3 shows a main configuration of the endoscope system according to Modification 1.

FIG. 3 shows a main configuration of the endoscope system 1 according to Modification 1. In FIG. 3, structures that are the same as those shown in FIG. 2 are specified by the same reference symbols as those in FIG. 2, and explanations thereof are omitted. Modification 1 is an example in which the sensor drive clock is used as the "clock synchronized with the video signal". In Modification 1, the video signal output from the CMOS sensor 121 is output in accordance with the transmission clock of the same frequency as that of the sensor drive clock (the sensor drive clock itself may be used).

In FIG. 3, the sensor drive clock generated by the sensor drive clock generation circuit 171 is input into the CMOS sensor 121 and also into the memory 172. The memory 172 stores the video signal from the CMOS sensor 121 in accordance with the input of the sensor drive clock and outputs the stored video signal to the image processor 22 in accordance with the input of the processor drive clock.

In the configuration of Modification 1, the sensor drive clock generation circuit 171 is used as the clock generation circuit for generating the "clock synchronized with the video signal". Thereby, it is possible to achieve substantially the same advantages as the embodiment described above without using a clock generation circuit for the "clock synchronized with the video signal".

Modification 2

Figure 4:
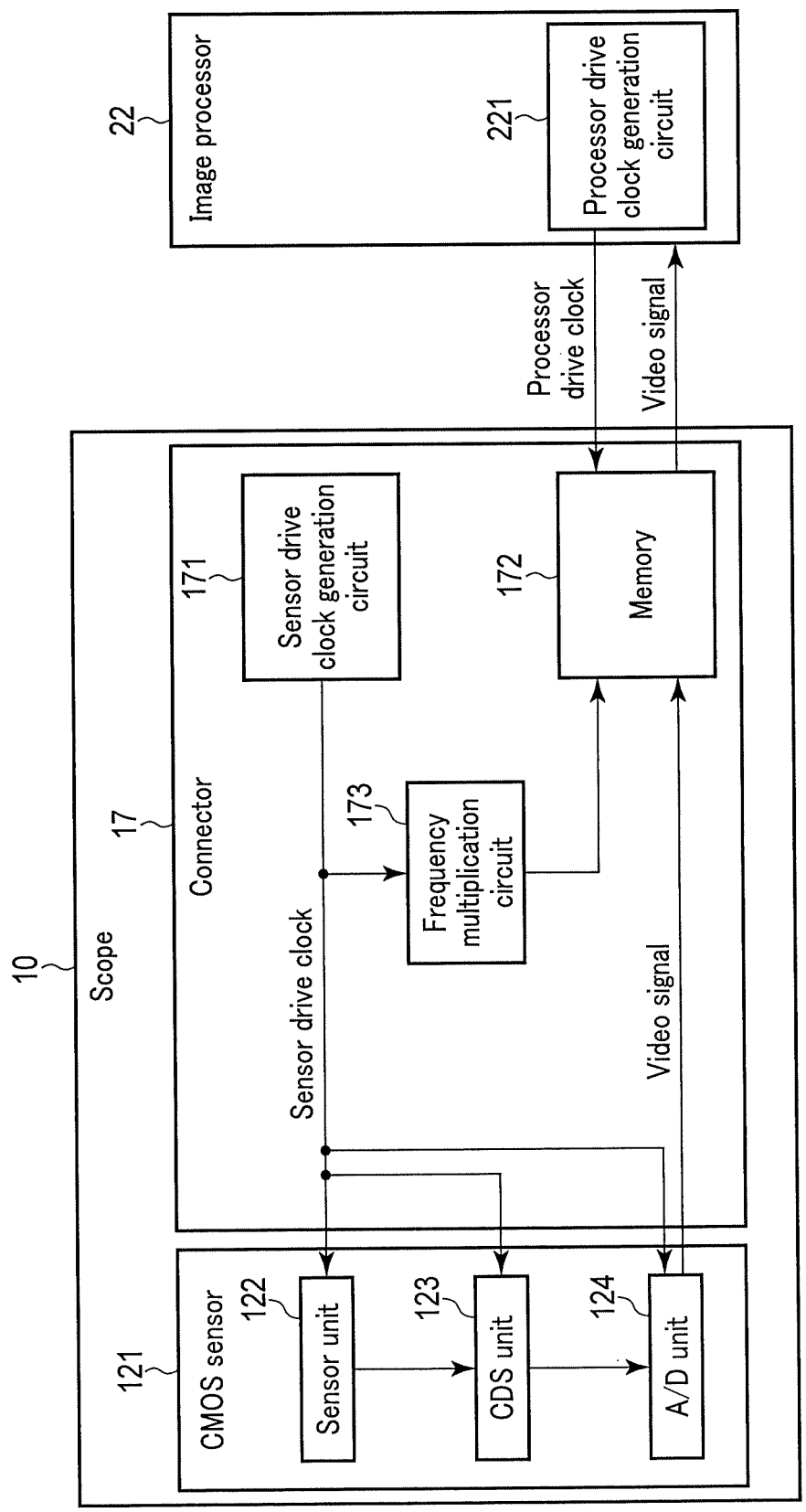
FIG. 4 shows a main configuration of the endoscope system according to Modification 2.

FIG. 4 shows a main configuration of the endoscope system 1 according to Modification 2. In FIG. 4, structures that are the same as those shown in FIG. 2 are specified by the same reference symbols as those in FIG. 2, and explanations thereof are omitted. Modification 2 is an example in which a clock generated by multiplying the sensor drive clock is used as the "clock synchronized with the video signal".

In FIG. 4, the sensor drive clock generated by the sensor drive clock generation circuit 171 is input into the CMOS sensor 121 and also into the frequency multiplication circuit 173. The frequency multiplication circuit 173 multiplies the frequency of the sensor drive clock to be matched to the frequency of the transmission clock of the video signal. The frequency multiplication circuit 173 then inputs the frequency-multiplied sensor drive clock to the memory 172. The memory 172 stores the video signal from the CMOS sensor 121 in accordance with the input of the frequency-multiplied sensor drive clock and outputs the stored video signal to the image processor 22 in accordance with the input of the processor drive clock.

In the configuration of Modification 2, the frequency multiplication circuit 173 is used as the clock generation circuit for generating the "clock synchronized with the video signal". Thereby, even if the frequency of the sensor drive clock and the frequency of the transmission clock of the video signal are not matched, it is possible to achieve substantially the same advantages as the embodiment described above. In Modification 2, the frequency multiplication circuit 173 is used as the clock generation circuit for generating the "clock synchronized with the video signal". A frequency divider circuit may be used as the clock generation circuit for generating the "clock synchronized with the video signal".

Modification 3

FIG. 5 shows a main configuration of the endoscope system 1 of Modification 3. In FIG. 5, structures that are the same as those shown in FIG. 2 are specified by the same reference symbols as those in FIG. 2, and explanations thereof are omitted. Modification 3 is an example in which the clock embedded in the video signal is used as the "clock synchronized with the video signal".

In FIG. 5, the video signal output from the CMOS sensor 121 is encoded while the clock synchronized with the video signal is embedded in this video signal. For the encoding method, an 8 B/10 B encoding method can be used, for example. The video signal encoded with the clock being embedded is input into a clock data recovery (CDR) circuit 174. The CDR circuit 174 divides the input video signal into a video signal and an extracted CDR clock, and inputs the divided video signal and CDR clock into the memory 172. The memory 172 stores the video signal from the CMOS sensor 121 in accordance with the input of the CDR clock from the CDR circuit 174 and outputs the stored video signal to the image processor 22 in accordance with the input of the processor drive clock.

In the configuration of Modification 3, the CDR circuit 174 is used as the clock generation circuit for generating the "clock synchronized with the video signal". Even in this case, it is possible to achieve substantially the same advantages as the embodiment described above even when the frequency of the sensor drive clock and the frequency of the clock synchronized with the video signal are not matched.

Modification 4

Figure 6:
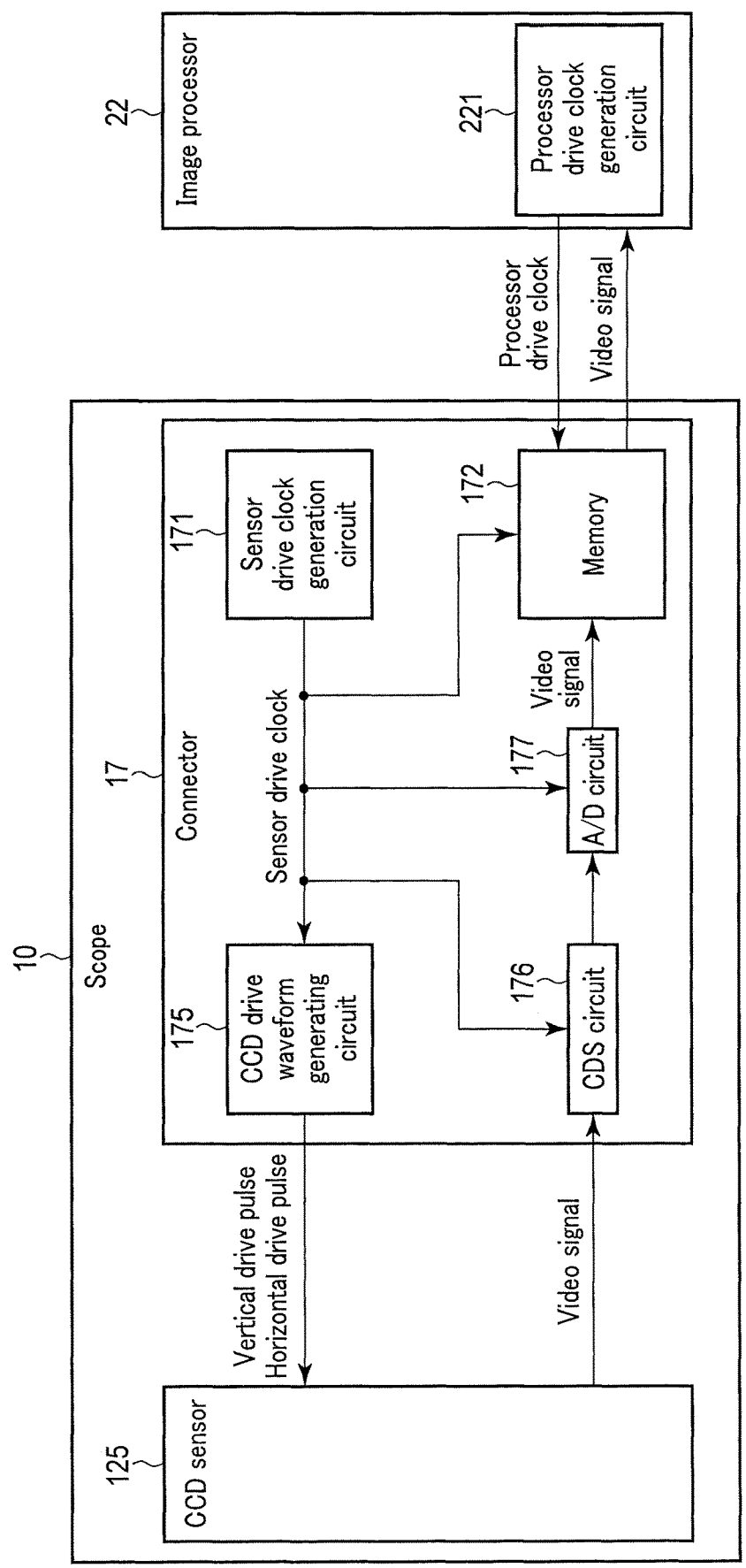
FIG. 6 shows a main configuration of the endoscope system according to Modification 4.

FIG. 6 shows a main configuration of the endoscope system 1 of Modification 4. In FIG. 6, structures that are the same as those shown in FIG. 2 are specified by the same reference symbols as those in FIG. 2, and explanations thereof are omitted. That is, Modification 4 is an example in which the imaging element 12 is a CCD sensor 125.

In FIG. 6, the sensor drive clock generated by the sensor drive clock generation circuit 171 is input into a CCD drive waveform generation circuit 175, a CDS circuit 176, an A/D circuit 177, and the memory 172.

The CCD drive waveform generation circuit 175 generates a vertical drive pulse and a horizontal drive pulse to drive the CCD sensor 125 from the sensor drive clock. The sensor unit of the CCD sensor 125 includes pixels formed by, for example, a photodiode, a vertical transfer unit (vertical CCD) that vertically transfers charges from the pixels, and a horizontal transfer unit (horizontal CCD) that horizontally transfers the vertically-transferred charges. The vertical drive pulse is a pulse for driving the vertical transfer unit. The vertical transfer unit transfers the charges sequentially toward the horizontal transfer unit each time it receives the vertical drive pulse. The horizontal drive pulse is a pulse for driving the horizontal transfer unit. The horizontal transfer unit outputs the video signal sequentially toward the CDS circuit 176 each time it receives the horizontal drive pulse.

The CDS circuit 176 is a circuit having functions similar to those of the CDS unit 123 in the CMOS sensor 121 and performs processing of removing a reset noise component (dark current component) in the video signal output from the sensor unit of the CCD sensor 125. The processing by the CDS circuit 176 is performed in synchronization with the sensor drive clock.

The A/D circuit 177 is a circuit having functions similar to those of the A/D unit 124 in the CMOS sensor 121 and converts the video signal output sequentially from the CDS unit 176 to a digital signal. The processing by the A/D circuit 177 is performed in synchronization with the sensor drive clock.

In FIG. 6, the memory 172 stores the video signal from the A/D circuit 177 in accordance with the input of the sensor drive clock input from the sensor drive clock generation circuit 171, and outputs the stored video signal to the image processor 22 in accordance with the input of the processor drive clock.

The configuration of Modification 4 achieves substantially the same advantages as the embodiment described above, even if the CCD sensor 125 is used as the imaging element 12. FIG. 6 shows an example in which Modification 1 described above is applied to a case where the CCD sensor 125 is used the imaging element 12. Modification 2 or 3 described above may be applied to the case where the CCD sensor 125 is used as the imaging element 12.

Modification 5

FIG. 7 shows a configuration of a connector 17 according to Modification 5. FIG. 7 shows only the configuration of the portion changed in the connector 17 from FIG. 2 to FIG. 6. For the structures not illustrated in FIG. 7, those illustrated in FIG. 2 to FIG. 6 apply.

Modification 5 is a modification of reading out the video signal from the memory 172. In Modification 5, the memory 172 is a parallel-output memory. The parallel video signal from the memory 172 is input into a parallel-to-serial conversion circuit 178 provided in the connector 17. The parallel-to-serial conversion circuit 178 converts the parallel video signal to a serial video signal and performs serial transmission to the image processor 22. The serial video signal is in synchronization with the processor drive clock.

According to the configuration of Modification 5, the video signal output from the parallel-output memory 172 is converted into a serial signal in the scope 10, thereby allowing serial transmission of the video signal from the scope 10 to the image processor 22.

Modification 6

Figure 8:
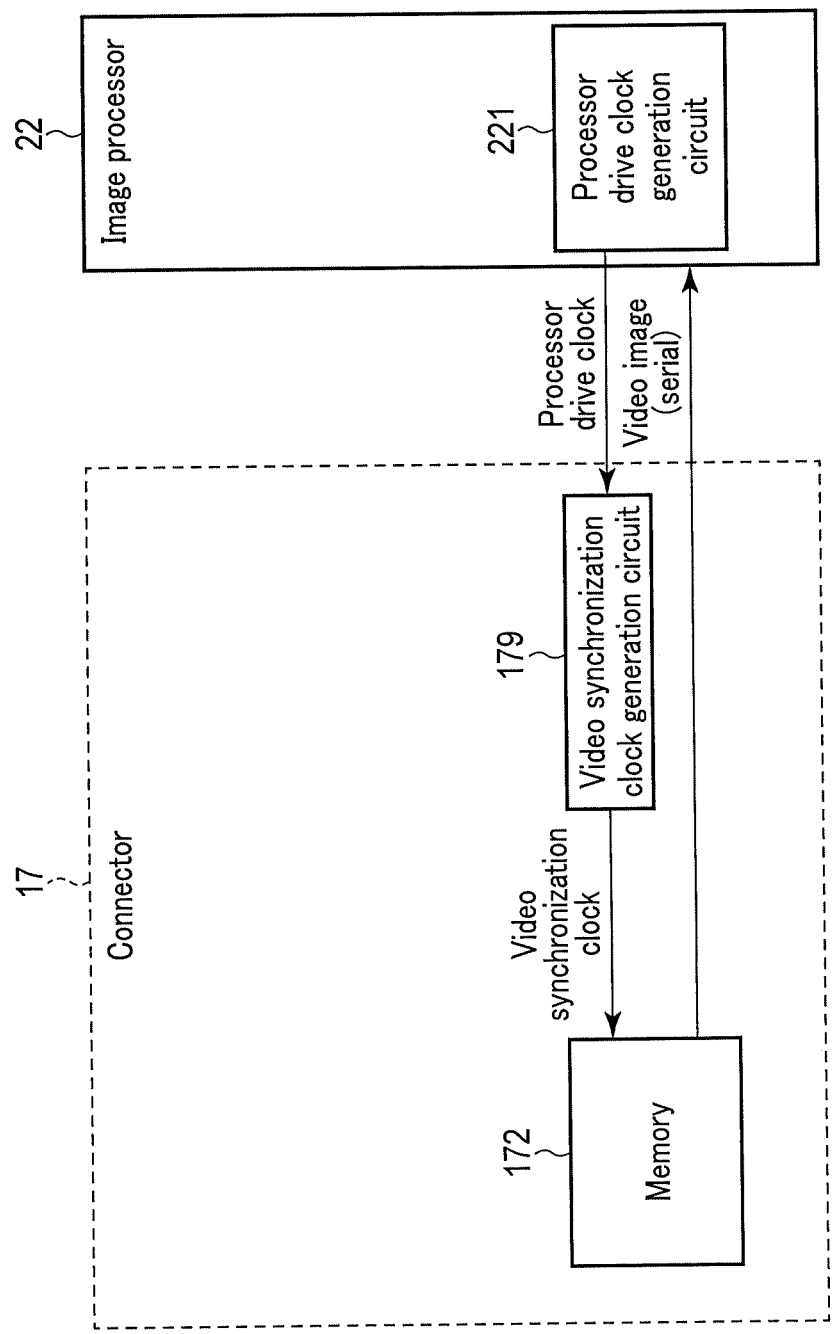
FIG. 8 shows a configuration of a connector according to Modification 6.

FIG. 8 shows a configuration of a connector 17 according to Modification 6. FIG. 8 shows only the configuration of the portion changed in the connector 17 from FIG. 2 to FIG. 6. For the structures not illustrated in FIG. 8, those illustrated in FIG. 2 to FIG. 6 apply.

Modification 6 is a modification of reading out the video signal from the memory 172. In Modification 6, the memory 172 is a serial-output memory.

In Modification 6, the processor drive clock from the processor drive clock generation circuit 221 of the image processor 22 is input into a video synchronization clock generation circuit 179 provided in the connector 17. The video synchronization clock generation circuit 179 generates a video synchronization clock for serially outputting the video signal from the memory 172. The video synchronization clock is generated by multiplying/dividing the processor drive clock. The memory 172 serially outputs the video signal upon receiving the video synchronization clock.

In the configuration of Modification 6, the clock for outputting the video signal from the serial-output memory 172 is generated from the processor drive clock. It is therefore possible to maintain synchronization between the imaging operation and the display operation even if the serial-output memory is used.

Other Modifications

In the above-described embodiment and modifications, the endoscope system has been discussed by way of example. The imaging apparatus (scope 10) of the present embodiment does not necessarily have to be inserted into the interior of the subject body. For example, the imaging apparatus of the present embodiment may be an extracorporeal camera that performs imaging from outside of the subject body. That is, the technique of the present embodiment is applicable to various systems that are carried out in synchronization with the clock in which the imaging operation of the imaging apparatus and the display operation of the processor are independent.

In this embodiment, the sensor drive clock generation circuit 171 and the memory 172, etc. are provided in the connector 17. The sensor drive clock generation circuit 171 and the memory 172, etc. do not necessarily have to be provided in the connector 17, and may be provided in any part of the scope 10.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
an image processor comprising hardware, wherein the image processor is configured to generate a processor drive clock for driving the image processor; and
a scope connected to the image processor, wherein the scope comprises:
  a connector configured to be connected to the image processor;
  an imaging element configured to output a video signal;
  a clock generation circuit configured to generate a sensor drive clock for driving the imaging element, wherein the sensor drive clock is generated independently of the processor drive clock;
  a memory for temporarily storing the video signal output from the imaging element, wherein the memory is configured to:
    store the video signal output from the imaging element in synchronization with the sensor drive clock; and
    output the stored video signal to the image processor via the connector in synchronization with the processor drive clock input from the image processor via the connector or a clock signal generated based on the processor drive clock; and
  a video synchronization clock generation circuit configured to generate a video synchronization clock based on the processor drive clock,
  wherein the memory is configured to serially output the video signal to the image processor in synchronization with the video synchronization clock.

2. The endoscope system of claim 1
wherein the clock generation circuit is configured to divide an encoded signal in which the sensor drive clock is embedded, into the video signal and the sensor drive clock.

3. The endoscope system of claim 1
wherein the imaging element comprises a complementary metal-oxide semiconductor (CMOS) sensor.

4. The endoscope system of claim 1
wherein the imaging element comprises a charge-coupled device (CCD) sensor.

5. The endoscope system of claim 1
wherein the memory is configured to perform parallel output of the video signal, and
wherein the endoscope system further comprises a parallel-to-serial conversion circuit that converts the video signal output from the memory to a serial signal.

6. The endoscope system of claim 1
wherein the clock generation circuit is provided in the connector.

7. The endoscope system of claim 1
wherein the memory is provided in the connector.

8. An endoscope system comprising:
an image processor comprising hardware, wherein the image processor is configured to generate a processor drive clock for driving the image processor; and
a scope connected to the image processor, wherein the scope comprises:
  a connector configured to be connected to the image processor;
  an imaging element configured to output a video signal;
  a clock generation circuit configured to generate a drive clock for driving the imaging element,
  a clock and data recovery circuit configured to divide the video signal, encoded in a state where a clock and data recovery (CDR) clock is embedded, into the video signal and the CDR clock, wherein the CDR clock is generated independently of the processor drive clock; and
  a memory for temporarily storing the video signal output from the imaging element, wherein the memory is configured to:
    store the video signal output from the imaging element in synchronization with the CDR clock; and
    output the stored video signal to the image processor via the connector in synchronization with the processor drive clock input from the image processor via the connector or a clock signal generated based on the processor drive clock.

9. The endoscope system of claim 8,
wherein the imaging element comprises a complementary metal-oxide semiconductor (CMOS) sensor.

10. The endoscope system of claim 8,
wherein the imaging element comprises a charge-coupled device (CCD) sensor.

11. The endoscope system of claim 8,
wherein the memory is configured to perform parallel output of the video signal, and
wherein the endoscope system further comprises a parallel-to-serial conversion circuit that converts the video signal output from the memory to a serial signal.

12. The endoscope system of claim 8,
wherein the clock generation circuit is provided in the connector.

13. The endoscope system of claim 8,
wherein the memory is provided in the connector.

* * * * *